US006287600B1

United States Patent
Ouali et al.

(10) Patent No.: US 6,287,600 B1
(45) Date of Patent: *Sep. 11, 2001

(54) STABILIZED PHARMACEUTICAL COMPOSITION OF A NONSTEROIDAL ANTI-INFLAMMATORY AGENT AND A PROSTAGLANDIN

(75) Inventors: Aomar Ouali, Montreal; Abul Kalam Azad, Pierrefonds, both of (CA)

(73) Assignee: Pharmascience Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/528,550

(22) Filed: Mar. 20, 2000

Related U.S. Application Data

(63) Continuation-in-part of application No. 09/273,692, filed on Mar. 22, 1999, now Pat. No. 6,183,779.

(51) Int. Cl.$^7$ ................ A61K 9/16; A61K 9/22; A61K 9/24; A61K 9/52; A61K 9/54
(52) U.S. Cl. ............ 424/472; 424/458; 424/468; 424/490; 514/772.3; 514/781; 514/951; 514/970
(58) Field of Search ................... 424/451, 452, 424/464, 465, 472, 489, 457, 458, 468, 490

(56) References Cited

U.S. PATENT DOCUMENTS

| | | | |
|---|---|---|---|
| 3,781,429 | 12/1973 | Partridge | 424/234 |
| 3,927,213 | 12/1975 | Lippman | 424/234 |
| 3,928,588 | 12/1975 | Robert | 424/234 |
| 3,954,787 | 5/1976 | Monkhouse | 260/308 D |
| 4,301,146 | 11/1981 | Sanvordeker | 424/80 |
| 5,015,481 | 5/1991 | Franz et al. | 424/494 |
| 5,601,843 | 2/1997 | Gimet et al. | 424/475 |
| 5,698,225 | 12/1997 | Gimet et al. | 424/475 |

FOREIGN PATENT DOCUMENTS

| | | |
|---|---|---|
| 91/16895 | 11/1991 | (WO) . |
| 99/12524 | 3/1999 | (WO) . |
| 99/65496 | 12/1999 | (WO) . |
| 00/01368 | 1/2000 | (WO) . |
| 00/15200 | 3/2000 | (WO) . |

OTHER PUBLICATIONS

Searle HealthNet Prescribing Information for Arthrotec® (downloaded from http://www.searlehealthnet.com/pi/arthrotec.html on Oct. 27, 1998).
Information for the Patient: Controtec™.

Primary Examiner—James M. Spear
(74) Attorney, Agent, or Firm—Dianne E. Reed; J. Elin Hartrum; Reed & Associates

(57) ABSTRACT

A pharmaceutical composition is provided for the oral administration of an NSAID and a prostaglandin. The composition is a solid dosage form wherein the NSAID is enterically coated and the prostaglandin is present along with an effective stabilizing amount of a prostaglandin stabilizing agent such as hydroxypropyl methylcellulose or polyvinylpyrrolidone. Exemplary dosage forms are bilayer tablets in which the prostaglandin is misoprostol and the NSAID is diclofenac, piroxicam, or a pharmaceutically acceptable salt thereof. Methods for using the composition to treat NSAID-responsive conditions, disorders and diseases are provided as well.

36 Claims, 1 Drawing Sheet

STABILIZED PHARMACEUTICAL COMPOSITION OF A NONSTEROIDAL ANTI-INFLAMMATORY AGENT AND A PROSTAGLANDIN

CROSS-REFERENCE To RELATED APPLICATIONS

This application is a Continuation-in-Part of U.S. patent application Ser. No. 09/273,692, filed Mar. 22, 1999 now U.S. Pat. No. 6,183,799, which patent application is incorporated herein by reference.

TECHNICAL FIELD

This invention relates generally to pharmaceutical compositions, and more particularly relates to a pharmaceutical composition containing a combination of a nonsteroidal anti-inflammatory drug (NSAID) and a prostaglandin.

BACKGROUND ART

Nonsteroidal anti-inflammatory agents such as diclofenac, difenpiramide, fenbufen, flufenamic acid, ibuprofen, indomethacin, ketoprofen, meclofenamate sodium, mefenamic acid, nabumetone, naproxen, piroxicam, suprofen and tiaprofenic acid, are widely used to relieve mild to moderate pain, for fever, and to treat inflammatory conditions. Sodium diclofenac, for example, is particularly effective for relief of musculoskeletal and joint disorders such as rheumatoid arthritis, an autoimmune disease, osteoarthritis and ankylosing spondilitis; periacicular disorders such as bursitis and tendinitis; soft-tissue disorders such as sprains and strains, and other painful conditions such as renal colic, acute gout, dysmenorrhoea, and for relieving pain following some surgical disorders. The NSAIDs are non-habit forming drugs and thus offer a significant advantage over traditional opioid-based drugs; furthermore, as NSAIDs are by definition "nonsteroidal," the side effects commonly associated with oral administration of steroids are avoided as well. However, it is recognized that NSAIDs also exhibit some undesirable side effects, particularly at high dosages and/or with chronic oral administration. Generally, high dosages and chronic use of NSAIDs are associated with problems such as gastrointestinal and duodenal bleeding, ulceration and perforation.

In view of the advantages of NSAIDs over opioid-based drugs and steroidal agents, steps have been undertaken to minimize the drugs' adverse effects. In one approach, NSAIDs have been administered locally, such as by injection, by topical administration of, for example, an ointment or cream, by use of a transdermal patch, or by an inhalation device. Although local administration is desirable, administration of an effective amount of the active agent is difficult or inconvenient. In another approach to reduce the adverse effects of NSAIDs, the agents are ingested after food or milk, or are taken in combination with antacids, histamine $H_2$-receptor antagonists, omeprazole, or sucralefate.

In yet another approach to reduce the undesirable gastrointestinal effects resulting from the oral administration of NSAIDs, the agents have been co-administered with some prostaglandins, particularly "E-series" prostaglandins such as $PGE_1$, $PGE_2$, misoprostol, and derivatives thereof; see, e.g., U.S. Pat. Nos. 3,781,429 to Partridge, 3,927,213 to Lippman, 3,928,588 to Robert, and 5,015,481 to Franz et al. Administration of a prostaglandin with an NSAID has been shown to reduce the ulcerogenicity of the NSAID. However, prostaglandins are unstable compounds and degrade readily in the presence of NSAIDs, thus requiring a stabilizing agent such as hydroxypropyl methylcellulose (HPMC) or polyvinylpyrrolidone (PVP) which can, in turn, lessen the activity of an NSAID. See, for example, U.S. Pat. No. 4,301,146 to Sanvordeker, which discloses prostaglandin E-type compounds stabilized with hydroxypropyl methylcellulose or polyvinylpyrrolidone before being pressed into tablets, U.S. Pat. No. 3,954,787 to Monkhouse, which discloses that lyophilized compositions of prostaglandin E and sodium chloride, cyclodextrin or polyvinylpyrrolidone are stable, and U.S. Pat. No. 5,015,481 to Franz et al., which discusses the destabilization of prostaglandins in the presence of the NSAIDs diclofenac and piroxicam.

There is, accordingly, a need in the art to provide a composition for administering an NSAID wherein the undesirable gastrointestinal side effects of the drug are minimized but wherein the drug's therapeutic effectiveness is maintained. The present invention is addressed to the aforementioned need in the art and provides a stabilized pharmaceutical composition of an NSAID and a prostaglandin, i.e., a composition in which the prostaglandin is stabilized and the efficacy of the NSAID is maintained.

DISCLOSURE OF THE INVENTION

Accordingly, it is a primary object of the invention to provide a stabilized pharmaceutical composition for oral administration of an NSAID and a prostaglandin.

It is another object of the invention to provide such a composition wherein the NSAID is enterically coated.

It is yet another object of the invention to provide such a composition that additionally includes a prostaglandin-stabilizing agent.

It is still another object of the invention to provide such a composition in which the enterically coated NSAID and the prostaglandin are present in discrete regions of the composition, such as in a bilayer tablet wherein the enterically coated NSAID is present in a first layer and the prostaglandin and the prostaglandin stabilizing agent are present in a second layer.

Another object of the invention is to provide a method for treating a patient with an NSAID-responsive condition, disease or disorder, wherein the method comprises administering an NSAID to the patient in a stabilized pharmaceutical composition as provided herein.

Still another object of the invention is to provide a method for reducing the undesirable gastrointestinal side effects associated with the oral administration of an NSAID, wherein the method comprises co-administering a prostaglandin with the NSAID in a stabilized pharmaceutical composition as provided herein.

Additional objects, advantages and novel features of the invention will be set forth in part in the description which follows, and in part will become apparent to those skilled in the art upon examination of the following, or may be learned by practice of the invention.

In one embodiment, the first layer of the bilayer tablet comprises an enterically coated nonsteroidal anti-inflammatory agent, and the second layer comprises a prostaglandin and a stabilizing agent.

In another embodiment, a method of treating a patient is provided for carrying out the present therapeutic method comprising administering to the patient a pharmaceutical composition bilayer tablet as described herein.

MODES FOR CARRYING OUT THE INVENTION

Figure 1:
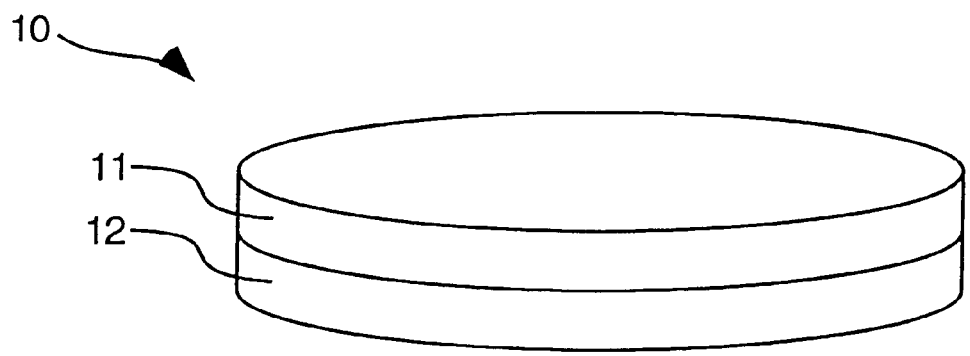
FIGS. 1 and 2 are schematic representations of dosage forms of the invention.

Overview and Definitions:

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a pharmacologically active agent" includes a combination of two or more pharmacologically active agents, reference to "a stabilizer" includes combinations of two or more stabilizers, reference to "a prostaglandin" includes combinations of two or more prostaglandins, and the like.

In describing and claiming the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect.

An "enterically coated" drug or tablet refers to a drug or tablet that is coated with a substance—i.e., with an "enteric coating"—that remains intact in the stomach but dissolves and releases the drug once the small intestine is reached.

By "pharmaceutically acceptable carrier" or "pharmaceutically acceptable vehicle" are meant materials that are suitable for oral administration and not biologically or otherwise undesirable, i.e., that may be administered to an individual along with an active agent without causing any undesirable biological effects or interacting in a deleterious manner with any of the other components of the pharmaceutical composition in which it is contained.

Similarly, a "pharmaceutically acceptable" salt, ester or other derivative of an active agent as provided herein is a salt, ester or other derivative which is not biologically or otherwise undesirable.

"Stabilizing agents" as used herein refer to compounds that lower the rate at which the prostaglandins degrade, particularly in an oral pharmaceutical formulation, in the presence of an NSAID, and under environmental conditions of storage.

By "incompatible," as in two drugs that are "incompatible" with respect to each other is meant that in close physical proximity a first drug may have a deleterious effect on the physical or chemical stability of a second drug, and/or vice versa.

By the terms "effective amount" or "therapeutically effective amount" of an agent as provided herein are meant a nontoxic but sufficient amount of the agent to provide the desired therapeutic effect. As will be pointed out below, the exact amount required will vary from subject to subject, depending on the age, weight, and general condition of the subject, the severity of the condition being treated, and the like. Thus, it is not possible to specify an exact "effective amount." However, an appropriate "effective" amount in any individual case may be determined by one of ordinary skill in the art using only routine experimentation.

By a "pharmacologically acceptable" compound is meant a material which is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmacologically acceptable" salt or a "pharmacologically acceptable" ester of a compound as provided herein is a salt or ester which is not biologically or otherwise undesirable.

Figure 2:
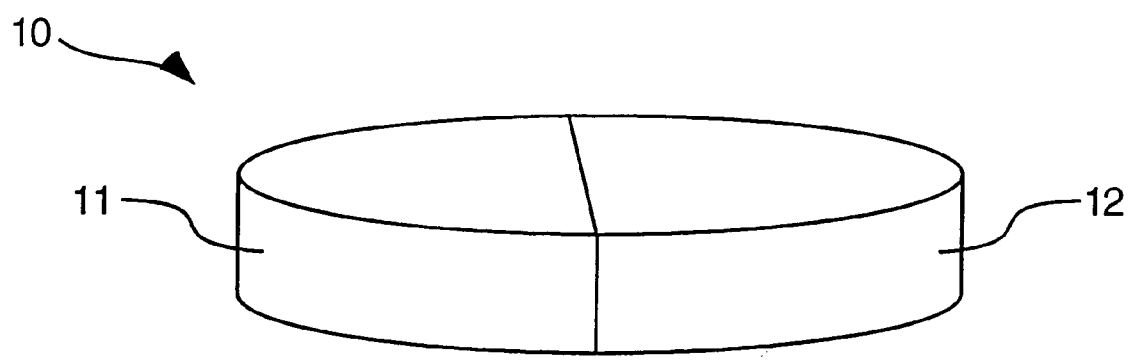

The invention, as noted above, is in one embodiment a stabilized pharmaceutical composition for administration of an NSAID and a prostaglandin, wherein the NSAID is enterically coated. Preferably, the composition is comprised of two discrete regions, wherein the enterically coated NSAID is present in a first region and the prostaglandin is present in a second region, along with a prostaglandin-stabilizing agent; an exemplary such composition is a bilayer tablet as shown in FIG. 1. The tablet 10 can have any geometric shape, although a generally oval shape is shown. The tablet 10 includes a first layer 11 and an adjacent second layer 12; alternatively, as shown in FIG. 2, the tablet can comprise a first region 13 adjacent to a second region 14.

The invention is not limited with respect to the selected NSAID; the stabilized compositions of the invention can contain any NSAID, NSAID derivative, or combination of NSAIDs. Typical NSAIDs include, but are not limited to, acetylsalicylic acid, apazone, diclofenac, difenpiramide, diflunisal, etodolac, fenbufen, flufenamic acid, flurbiprofen, ibuprofen, indomethacin, ketoprofen, ketorolac, meclofenamate, mefenamic acid, nabumetone, naproxen, oxaprozin, piroxicam, sulindac, suprofen, tiaprofenic acid and tolmetin. Pharmaceutically acceptable analogs of such NSAIDs are suitable as well, particularly pharmaceutically acceptable salts. Diclofenac, piroxicam and their salts (e.g., diclofenac sodium) are particularly preferred.

The NSAID is present in the composition in a therapeutically effective amount; preferably, the composition is in unit dosage form. The amount of NSAID administered will, of course, be dependent on the age, weight, and general condition of the subject, the severity of the condition being treated, and the judgment of the prescribing physician. Suitable therapeutic amounts will be known to those skilled in the art and/or are described in the pertinent reference texts and literature. For diclofenac sodium, for example, a therapeutic dose is typically in the range of approximately 25 mg to about 75 mg per tablet, optimally about 50 mg per tablet. The therapeutic dosing range for a tablet containing piroxicam is about 5 mg to about 50 mg per tablet, optimally about 20 mg per tablet, while the therapeutic dosing range for a tablet containing naproxen is about 250 mg to 750 mg per tablet.

The NSAID is enterically coated within the stabilized composition of the invention. Generally, the enteric coating comprises a polymeric material that prevents NSAID release in the low pH environment of the stomach but that ionizes at a slightly higher pH, typically a pH of 4 or 5, and thus dissolves sufficiently in the small intestines to gradually release the active agent therein. Accordingly, among the most effective enteric coating materials are polyacids having a $pK_a$ in the range of about 3 to 5. Suitable enteric coating materials include, but are not limited to, polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (UPMCAS), and acrylic acid polymers and copolymers, preferably formed from methyl acrylate, ethyl acrylate, methyl methacrylate and/or ethyl methacrylate with copolymers of acrylic and methacrylic acid esters (Eudragit NE, Eudragit RL, Eudragit RS) particularly preferred.

The NSAID-containing region or layer can also contain various excipients, as is well known in the pharmaceutical art, provided such excipients do not exhibit a destabilizing effect on any components in the composition. Thus, excipients such as binders, bulking agents, diluents, disintegrants, lubricants, fillers, carriers, and the like can be combined with the NSAID in the core. For solid compositions, diluents are typically necessary to increase the bulk of a tablet so that a practical size is provided for compression. Suitable diluents include dicalcium phosphate, calcium sulfate, lactose, cellulose, kaolin, mannitol, sodium chloride, dry starch and powdered sugar. Binders are used to impart cohesive qualities to a tablet formulation, and thus ensure that a tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, and the like), and Veegum. Lubricants are used to facilitate tablet manufacture; examples of suitable lubricants include, for example, magnesium stearate, calcium stearate, and stearic acid, and are preferably present at no more than approximately 1 wt. % relative to tablet weight. Disintegrants are used to facilitate tablet disintegration or "breakup" after administration, and are generally starches, clays, celluloses, algins, gums or crosslinked polymers. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. If desired, flavoring, coloring and/or sweetening agents may be added as well. Other optional components for incorporation into an oral formulation herein include, but are not limited to, preservatives, suspending agents, thickening agents, and the like. Fillers include, for example, insoluble materials such as silicon dioxide, titanium oxide, alumina, talc, kaolin, powdered cellulose, microcrystalline cellulose, and the like, as well as soluble materials such as mannitol, urea, sucrose, lactose, dextrose, sodium chloride, sorbitol, and the like.

The second region or layer of the composition contains a prostaglandin to reduce or eliminate the undesirable side effects of the NSAID following oral administration. Thus, preferred prostaglandins are those which are effective in this regard, i.e. are typically "antiulcerogenic." The prostaglandin is selected from the group consisting of naturally occurring prostaglandins, derivatives of naturally occurring prostaglandins such as hydrolyzable lower alkyl esters thereof, synthetic prostaglandins and semisynthetic prostaglandins.

The "naturally occurring" prostaglandins useful in conjunction with the present invention are $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$ and $PGI_2$. The term "synthetic prostaglandin derivatives" is intended to encompass known or unknown compounds related to the aforementioned naturally occurring prostaglandins that are chemically synthesized using starting materials other than one of the naturally occurring prostaglandins. The term "semisynthetic prostaglandin derivatives" refers to known or unknown compounds related to the aforementioned naturally occurring prostaglandins and that are synthesized therefrom. Synthetic and semisynthetic prostaglandins include, but are not limited to, carboprost tromethamine, dinoprost tromethamine, dinoprostone, lipoprost, gemeprost, metenoprost, sulprostone and tiaprost. The preferred prostaglandin is misoprostol, present in an amount of about 50 to 500 µg per tablet, more preferably about 100 to 200 µg per tablet. Misoprostol is released immediately in the gastrointestinal tract, and produces its gastric anti-secretory effect thereby effectively reducing and/or eliminating the ulcerogenocity of the NSAID.

The region or layer of the present pharmaceutical composition containing the prostaglandin also contains a prostaglandin stabilizing agent such as hydroxypropyl methylcellulose or polyvinylpyrrolidone, as disclosed in U.S. Pat. No. 4,301,146 to Sanvordeker. Other stabilizing agents include, but are not limited to: cellulosic polymers such as hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose phthalate, microcrystalline cellulose and carboxymethylcellulose sodium; and vinyl polymers and copolymers such as polyvinyl acetate, polyvinylacetate phthalate, vinylacetate crotonic acid copolymer, and ethylene-vinyl acetate copolymers. The stabilizing agent is present in an amount effective to provide the desired stabilizing effect; generally, this means that the ratio of prostaglandin to the prostaglandin stabilizing agent is at least about 1:500 w/w, more preferably about 1:99 w/w.

The prostaglandin-containing region or layer can also contain various excipients, as discussed with respect to the NSAID-containing region or layer, i.e., excipients that do not exhibit a destabilizing effect and include, for example, binders, bulking agents, diluents, disintegrants, lubricants, fillers, carriers, and the like.

The active agents in the present composition, i.e., both the NSAID and the prostaglandin, may be administered in the form of a pharmacologically acceptable salt, ester, amide, prodrug or analog or as a combination thereof. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

Before incorporation into a dosage form, the NSAID is preferably provided in a particulate form suitable for processing. Preferred types of particles are selected from the group consisting of granules, pellets, seeds and microspheres. Granules may be prepared by any art-known process. It is preferred, however, that the granules be prepared by processes such as high shear granulation, low shear granulation or fluid-bed granulation provided with top spray. Pellets or seeds can be prepared by techniques known to those skilled in the art, for example, by using a fluid-bed granulator provided with a rotor-disc. Microspheres can be prepared by any art known process with preparation by spray drying preferred.

Once in particulate form, the NSAID is enterically coated. Although any art-known process may be used, it is preferred that the enteric coating process be accomplished by utilizing either a fluid-bed coater provided with a top spray or a fluid-bed Wurster coater with a bottom spray. The resulting enterically coated particles should have a particle size in the range of about 20 µm to 1500 µm, preferably in the range of about 50 µm to 300 µm.

Before incorporation into the dosage form, the prostaglandin should be separately stabilized with the stabilizing agent. Suitable stabilization procedures are well known to those skilled in the art.

One preferred dosage form of the present invention is a bilayer tablet. Bilayer tablets as shown in FIGS. 1 and 2 provide several manufacturing advantages. The bilayer tablet is made in a single step compression, thereby eliminating the operations of prior methods involving first compressing one of the actives as a core tablet and subsequently coating the core, and additionally eliminating the concomitant steps of in-process and quality controls for manufacturing two different tablets. Thus, the bilayer tablet is easier and more economical to manufacture than prior compositions that separate a first drug and a second drug into physically discrete regions of a single dosage form.

A preferred method for forming tablets herein is by direct compression of the enterically coated NSAID and prostaglandin, optionally in combination with diluents, binders, lubricants, disintegrants, colorants or the like. As an alternative to direct compression, compressed tablets can be prepared using wet-granulation or dry-granulation processes. Tablets may also be molded rather than compressed, starting with a moist material containing a suitable water-soluble lubricant. Preferred tablets herein are manufactured using compression rather than molding, however.

In an alternative embodiment, the enterically coated NSAID and the stabilized prostaglandin are mixed into a single granulation, and the admixture is compressed into a tablet or filled into a capsule. In the admixture, there is a random possibility of the NSAID and the prostaglandin coming into contact with each other. However, the enteric coating on the NSAID granules provides a physical barrier between the NSAID and the prostaglandin, thereby minimizing direct physical contact between the two active agents. Capsule materials may be either hard or soft, and are preferably sealed, such as with gelatin bands or the like. Tablets and capsules for oral use will generally include one or more commonly used excipients as discussed earlier herein.

For administration of the dosage form, i.e., the tablet or capsule containing the enterically coated NSAID and the stabilized prostaglandin, a total weight in the range of approximately 100 mg to 1000 mg is used. The dosage form is orally administered to a patient suffering from a condition for which an NSAID would typically be indicated, including, but not limited to: alleviation of pain, e.g., arthritic pain, lumbosacral pain, musculo-skeletal pain, pain associated with a sore throat, and the like; treatment of inflammatory conditions and diseases such as osteoarthritis and rheumatoid arthritis; and treatment of psoriasis.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

A misoprostol-HPMC complex 1% was made by mixing misoprostol with HPMC in a ratio of 1:99. Misoprostol, an oily, viscous liquid was stabilized as a solid dispersion using hydroxypropyl methycellulose as substrate and spraying misoprostol from an alcoholic solution in a fluid-bed granulator. The granules so obtained were mixed with excipients as described in Example 2.

EXAMPLE 2

The granules of the misoprostol-HPMC complex prepared in Example 1 were mixed with the following excipients.

| Ingredient | mg per 200 mg |
|---|---|
| Misoprostol-HPMC Complex 1% | 20.0 |
| Microcrystalline Cellulose PH 102 | 141.8 |
| Crospovidone XL | 8.0 |
| Microcrystalline Cellulose PH 102 | 29.0 |
| Hydrogenated Castor Oil Powder | 0.8 |
| Colloidal Silicon Dioxide | 0.4 |

The blend so obtained was used in the preparation of the bilayer tablets as described in Examples 5 and 6 below.

EXAMPLE 3

A blend of enterically coated granules of diclofenac was prepared as follows.

| Ingredient | mg per 200 mg |
|---|---|
| Granulation I | |
| Diclofenac Sodium | 50.0 |
| Lactose Hydrous Spray Dried | 15.0 |
| Microcrystalline Cellulose PH 102 | 16.0 |
| Starch (Corn) Tablet White | 9.0 |
| Povidone PVK-30 | 4.0 |
| Granulation II | |
| Methacrylic Acid Copolymer Type C | 5.4 |
| Triacetin | 0.54 |
| Antifoam 1520-US | 0.06 |
| Microstalline Cellulose PH 102 | 98 |
| Hydrogenated Castor Oil Powder | 2 |

In the first step, granulation I was prepared by blending diclofenac sodium with lactose hydrous spray dried, microcrystalline cellulose PH 102, starch (corn) tablet white, and an aqueous solution of Povidone PVK-30 in a fluid-bed granulator. The granules so obtained were enteric coated in a fluid-bed granulator by the application of an enteric dispersion system containing methacrylic acid copolymer type C, NF, triacetin, and antifoam 1520-US. The enterically coated diclofenac granules were then blended with microcrystalline cellulose PH 102 and hydrogenated castor oil powder.

EXAMPLE 4

A second composition of the diclofenac layer for the pharmaceutical delivery system of bilayer tablet was prepared consisting of enterically coated granules of diclofenac. The tablet had the following composition, and the excipients were blended according to Example 3.

| Ingredient | mg per 200 mg |
|---|---|
| Granulation I | |
| Diclofenac Sodium | 50.0 |
| Lactose Hydrous Spray Dried | 15.0 |
| Microcrystalline Cellulose PH 102 | 18.0 |
| Starch (Corn) Tablet White | 9.0 |
| Povidone PVK-30 | 4.0 |
| Granulation II | |
| Methacrylic Acid Copolymer Type C | 2.70 |
| Triacetin | 0.27 |
| Antifoam 1520-US | 0.03 |
| Hydrogenated Castor Oil Powder | 1.0 |

EXAMPLE 5

A bilayer tablet was prepared containing a misoprostol solid dispersion and enterically coated granules of diclofenac. The enterically coated NSAID prepared in Example 3 was first placed in the tablet press, followed by the misoprostol blend prepared in Example 2. The tableting mechanism was then actuated to give a bilayer tablet.

EXAMPLE 6

The misoprostol blend, prepared in Example 2, is mixed with the diclofenac blend prepared in either Example 3 or Example 4. The admixture so obtained is compressed into a tablet, or is filled into a capsule shell.

What is claimed is:

1. A solid pharmaceutical composition for oral administration, comprising:
    a therapeutically effective amount of enterically coated particles of a nonsteroidal anti-inflammatory drug (NSAID) having a particle size in the range of about 50 $\mu$m to about 300 $\mu$m;
    an effective anti-ulcerogenic amount of a prostaglandin; and
    an effective stabilizing amount of a prostaglandin stabilizing agent.

2. The composition of claim 1, comprising a dosage form having two discrete regions, wherein the enterically coated NSAID is present in the first of said two regions and the prostaglandin and prostaglandin stabilizing agent are present in the second of said two regions.

3. The composition of claim 2, comprising a bilayer tablet.

4. The composition of claim 2, comprising a capsule.

5. The composition of claim 1, comprising an admixture of the enterically coated NSAID, prostaglandin and prostaglandin stabilizing agent.

6. The composition of claim 5, in the form of a tablet.

7. The composition of claim 1, wherein the NSAID is selected from the group consisting of acetylsalicylic acid, apazone, diclofenac, difenpiramide, diflunisal, etodolac, fenbufen, flufenamic acid, flurbiprofen, ibuprofen, indomethacin, ketoprofen, ketorolac, meclofenamate, mefenamic acid, nabumetone, naproxen, oxaprozin, piroxicam, sulindac, suprofen, tiaprofenic acid, tolmetin, pharmaceutically acceptable salts thereof, and combinations of any of the foregoing.

8. The composition of claim 7, wherein the NSAID is diclofenac or a pharmaceutically acceptable salt thereof.

9. The composition of claim 8, wherein the NSAID is diclofenac.

10. The composition of claim 8, wherein the NSAID is diclofenac sodium.

11. The composition of claim 7, wherein the NSAID is piroxicam.

12. The composition of claim 1, wherein the prostaglandin is selected from the group consisting of misoprostol, $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$, $PGI_2$, carboprost tromethamine, dinoprost tromethamine, gemeprost, metenoprost, sulprostone, tiaprost and combinations thereof.

13. The composition of claim 12, wherein the prostaglandin is misoprostol.

14. The composition of claim 1, wherein the prostaglandin stabilizing agent is selected from the group consisting of hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose, hydroxypropyl methylcellulose phthalate, microcrystalline cellulose, carboxymethylcellulose sodium, polyvinylpyrrolidone, polyvinyl acetate, polyvinylacetate phthalate, and vinylacetate crotonic acid copolymer, and combinations thereof.

15. The composition of claim 14, wherein the stabilizing agent is hydroxypropyl methylcellulose.

16. The composition of claim 14, wherein the stabilizing agent is polyvinylpyrrolidone.

17. A bilayer tablet for oral administration of a nonsteroidal anti-inflammatory drug (NSAID), comprising:
    (a) a first layer containing a therapeutically effective amount of enterically coated NSAID particles having a particle size ranging from about 50 $\mu$m to about 300 $\mu$m, selected from the group consisting of acetylsalicylic acid, apazone, diclofenac, difenpiramide, diflunisal, etodolac, fenbufen, flufenamic acid, flurbiprofen, ibuprofen, indomethacin, ketoprofen, ketorolac, meclofenamate, mefenamic acid, nabumetone, naproxen, oxaprozin, piroxicam, sulindac, suprofen, tiaprofenic acid, tolmetin, pharmaceutically acceptable salts thereof, and combinations of any of the foregoing; and
    (b) a second layer containing an effective anti-ulcerogenic amount of a prostaglandin selected from the group consisting of misoprostol, $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$, $PGI_2$, carboprost tromethamine, dinoprost tromethamine, gemeprost, metenoprost, sulprostone, tiaprost and combinations thereof, and an effective stabilizing amount of a prostaglandin stabilizing agent selected from the group consisting of hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose, hydroxypropyl methylcellulose phthalate, microcrystalline cellulose, carboxymethylcellulose sodium, polyvinylpyrrolidone, polyvinyl acetate, polyvinylacetate phthalate, and vinylacetate crotonic acid copolymer, and combinations thereof.

18. A bilayer tablet for oral administration of a nonsteroidal anti-inflammatory drug (NSAID), comprising:
   (a) a first layer containing a therapeutically effective amount of enterically coated NSAID particles having a particle size ranging from about 50 $\mu$m to about 300 $\mu$m, selected from the group consisting of diclofenac, piroxicam, naproxen and pharmaceutically acceptable salts thereof; and
   (b) a second layer containing an effective anti-ulcerogenic amount of misoprostol and an effective stabilizing amount of a prostaglandin stabilizing agent selected from the group consisting of hydroxypropyl methylcellulose and polyvinylpyrrolidone.

19. The composition of claim 1, wherein the particles are selected from the group consisting of granules, pellets, seeds and microspheres.

20. The composition of claim 19, wherein the particles are granules.

21. The composition of claim 1, wherein the total weight of the composition is in the range of approximately about 100 mg to about 1000 mg.

22. The composition of claim 21, wherein the amount of prostaglandin is in the range of approximately about 5 $\mu$g to about 500 $\mu$g.

23. The bilayer tablet of claim 17, wherein the particles are selected from the group consisting of granules, pellets, seeds and microspheres.

24. The bilayer tablet of claim 23, wherein the particles are granules.

25. The tablet of claim 18, having a total weight in the range of approximately 100 mg to 1000 mg.

26. The tablet of claim 25, containing approximately 25 mg to 75 mg diclofenac.

27. The tablet of claim 25, containing approximately 5 mg to 50 mg piroxicam.

28. The tablet of claim 25, containing approximately 250 mg to 750 mg naproxen.

29. The tablet of claim 25, containing approximately 100 $\mu$g to 200 $\mu$g misoprostol.

30. A tablet comprising an admixture of (a) a therapeutically effective amount of enterically coated NSAID particles having a particle size ranging from about 50 $\mu$m to about 300 $\mu$m, selected from the group consisting of diclofenac, piroxicam and pharmaceutically acceptable salts thereof; (b) an effective anti-ulcerogenic amount of misoprostol; and (c) an effective stabilizing amount of a prostaglandin stabilizing agent selected from the group consisting of hydroxypropyl methyl cellulose and polyvinylpyrrolidone.

31. A method for treating a patient suffering from a condition, disease or disorder that is responsive to an NSAID, comprising orally administering to the patient the pharmaceutical composition of any one of claims 1, 17, 18, or 30.

32. The method of claim 31, wherein the composition is administered twice daily.

33. The bilayer tablet of claim 18, wherein the particles are selected from the group consisting of granules, pellets, seeds and microspheres.

34. The bilayer tablet of claim 33, wherein the particles are granules.

35. The tablet of claim 30, wherein the particles are selected from the group consisting of granules, pellets, seeds and microspheres.

36. The tablet of claim 35, wherein the particles are granules.

* * * * *